(12) United States Patent
Matsumori

(10) Patent No.: US 7,989,174 B2
(45) Date of Patent: Aug. 2, 2011

(54) BIOMARKER FOR DIAGNOSING HEART DISEASE AND THE USE THEREOF

(76) Inventor: Akira Matsumori, Minoh (JP)

( * ) Notice: Subject to any disclaimer, the term of this patent is extended or adjusted under 35 U.S.C. 154(b) by 0 days.

(21) Appl. No.: 12/813,892

(22) Filed: Jun. 11, 2010

(65) Prior Publication Data
US 2010/0291587 A1 Nov. 18, 2010

Related U.S. Application Data

(62) Division of application No. 11/911,283, filed as application No. PCT/JP2006/307631 on Apr. 11, 2006, now Pat. No. 7,781,178.

(30) Foreign Application Priority Data

Apr. 12, 2005 (JP) ................................ 2005-114350

(51) Int. Cl.
G01N 33/53 (2006.01)
(52) U.S. Cl. ........................ 435/7.1; 435/7.2; 436/518
(58) Field of Classification Search ................. None
See application file for complete search history.

(56) References Cited

U.S. PATENT DOCUMENTS 4,800,155 A 1/1989 Taniguchi et al.

OTHER PUBLICATIONS

Fisher, Christian et al., "Kappa Free Light Chains in Cerebrospinal Fluid as Markers of Intrathecal Immunoglobulin Synthesis", Clinical Chemistry, vol. 50, No. 10, pp. 1809-1813, 2004.
Katzmann, Jerry A. et al., "Serum Reference Intervals and Diagnostic Ranges for Free K and Free Λ Immunoglobulin Light Chains: Relative Sensitivity for Detection of Monoclonal Light Chains", Clinical Chemistry, vol. 48, No. 9, pp. 1437-1444, 2002.
Bollengier, Francine, "Bound and Free Light Chains in Serum from Patients Affected with Various Neurological Diseases", J. Clin. Chem.Clin.Biochem., vol. 17, pp. 45-49, 1979.
Contini, Carlo et al., "Evidence of Cerebrospinal Fluid Free Kappa Light Chains in AIDS patients with Toxoplasma gondii encephalitis", Journal of Neuroimmunology, vol. 108, pp. 221-226, 2000.
Dubrey S.W., et al., "The clinical features of Immunoglobulin light-chain (AL) amyloidosis with heart involvement", Monthly Journal of the Association of Physicians, vol. 91, No. 2, Feb. 1998, p. 141-157.
Sanchorawala, Vaishali, et al., "Pulsed Low Dose Intravenous Melphalan in Patients with AL Amyloidosis, Ineligible for Aggressive Treatment with High-Dose Melphalan and Stem Cell Transplantation", Blood (ASH Annual Meeting Abstracts), vol. 4, No. 11, Part 1, Nov. 2004.
Hsu, J.Y., et al., "The Clinicopathological Specturm of Renal Amyloidosis", Zhonghua Yi Xue Za Zhi = Chinese Medical Journal; Free China ed, vol. 54, No. 4, Oct. 1994, pp. 230-239.
Burkhardt, O., et al., "Diagnosis of multiple myeloma by demonstrating plasma cells in bronchoalveolar lavage", DMW Deutsche Medizinische Wochenschrift, vol. 128, No. 38, Sep. 19, 2003, pp. 1951-1954.
Nakano, T., et al., "Elisas for free human immuniglobulin light chains in serum: improvement of assay specificity by using two specific antibodies in a sandwich detection method", Journal of Immunological Methods, vol. 293, No. 1-2, Oct. 1, 2004, pp. 183-189.
"Free Immunoglobulin Light-Chains as a New Biomarker of Heart Failure" Journal of Cardial Failure, vol. 11, No. 6, Aug. 1, 2005, p. S121.
Falk, Rodney H., "Diagnosis and Management of the Cardiac Amyloidoses", Circulation, vol. 112, No. 13, Sep. 27, 2005, pp. 2047-2060.
Motoyuki Nakamura, et al., "Reversible Restrictive Cardiomyopathy Due to Light-Chain Deposition Disease", Mayo Clin Proc., Mayo Foundation for Medical Education and Research, vol. 77, Feb. 2002, pp. 193-196.
Wong et al., Cardiovascular Pathology 2004, vol. 13, p. 49-53.
Garton et al., Postgrad Med J, 1993, vol. 69, pp. 588-591.
Kyriakides et al., Clinical neuropath, 2001, vol. 21, pp. 145,148.

*Primary Examiner* — Jacob Cheu
(74) *Attorney, Agent, or Firm* — Oblon, Spivak, McClelland, Maier & Neustadt, L.L.P.

(57) ABSTRACT

The invention relates to the following methods [1] to [3] and to a kit for carrying out the methods:

[1] a method for detecting heart disease, characterized in that the method comprises determining a free immunoglobulin kappa light chain level and/or a free immunoglobulin lambda light chain level of a specimen and comparing at least one value of the kappa chain level, the lambda chain level, and a kappa/lambda ratio with that of a healthy subject;

[2] a method for detecting a complication of viral infection in a patient with heart disease, characterized in that the method comprises determining a free immunoglobulin kappa light chain level and/or a free immunoglobulin lambda light chain level of a specimen and comparing at least one value of the kappa chain level, the lambda chain level, and a kappa/lambda ratio with that of a healthy subject;

[3] A method for detecting severity of heart disease, characterized in that the method comprises determining a free immunoglobulin kappa light chain level and/or a free immunoglobulin lambda light chain level of a specimen and comparing at least one value of the kappa chain level, the lambda chain level, and a kappa/lambda ratio with that of a healthy subject or a patient suffering slight heart disease.

12 Claims, 1 Drawing Sheet

BIOMARKER FOR DIAGNOSING HEART DISEASE AND THE USE THEREOF

CROSS-REFERENCE TO RELATED APPLICATIONS

This application is a divisional of U.S. application Ser. No. 11/911,283 filed Oct. 11, 2007, now U.S. Pat. No. 7,781,178, which is a 371 of PCT/JP2006/307631 filed Apr. 11, 2006 and claims the benefit of JP 2005-114350 file Apr. 12, 2005.

TECHNICAL FIELD

The present invention relates to a novel biomarker for diagnosis of heart disease and to use thereof.

BACKGROUND ART

Generally, heart failure is defined as a pathological condition in which heart function is deteriorated by various conditions such as an ischemic heart disease (e.g., myocardial infarction or angina pectoris), cardiomyopathy, or hypertension. Currently available biomarkers for diagnosing such a heart failure include atrial natriuretic peptide (ANP), brain natriuretic peptide (BNP), and N-terminal proBNP (NT-proBNP). Assaying such a marker can determine whether or not a patient suffers from heart failure, and how severe the heart failure is.

However, since the cause of many diseases including heart failure cannot be determined as a single factor, in actual clinical settings a specific disease cannot be definitely diagnosed through assaying only one type of biomarker. In addition, since they are found in blood, urine, etc. in response to progress of pathological conditions, biomarkers may fail to specifically diagnose the target pathological conditions when the progress of the conditions varies among individual patients. Therefore, currently, many diseases are generally diagnosed by use of a variety of markers in combination.

DISCLOSURE OF THE INVENTION

Problems to be Solved by the Invention

Thus, for the diagnosis of heart diseases such as heart failure, keen demand exists for development of a novel marker other than known markers such as ANP and BNP.

Means for Solving the Problems

The present inventor has carried out extensive studies in an attempt to develop a novel biomarker for diagnosing heart disease, and has paid attention to a free immunoglobulin light chain dissociated from an immunoglobulin heavy chain (i.e., free light chain (FLC)), which has never been employed for the diagnosis of heart disease.

Hitherto, FLC assay has been employed for the diagnosis of blood diseases such as myeloma and amyloidosis. In myeloma, FLC assay results vary depending on the type of tumor cells. Specifically, when the tumor cells produce kappa (κ) chains, the kappa chain level and the kappa/lambda ratio increase, whereas when the tumor cells produce lambda (λ) chains, the lambda chain level increases and the kappa/lambda ratio decreases. The type of myeloma has been diagnosed on the basis of the assay characteristics.

The aforementioned FLC is a type of pathological condition markers and is conceived to be a marker which indicates the activation of B lymphocytes. Therefore, if FLC can be employed for the diagnosis of heart failure, activation of B lymphocytes can possibly be detected in the diagnosis of heart failure. If the activation can be detected, screening and development of a novel heart failure therapeutic drug can be attained through regulating activation of B lymphocytes. Thus, FLC is a promising candidate for a useful marker, which differs from conventional markers.

The present inventor has further carried out extensive studies on application of FLC to the diagnosis of heart disease, and have found that FLC, which has never been employed for the diagnosis of heart disease, can be applied to the diagnosis of heart disease including heart failure. The present invention has been accomplished on the basis of this finding. Accordingly, the present invention is directed to the following.

[1] A method for detecting heart disease, characterized in that the method comprises determining a free kappa light chain level and/or a free lambda light chain level of a specimen and comparing at least one value of the kappa chain level, the lambda chain level, and a kappa/lambda ratio with that of a healthy subject.

[2] A method for detecting a complication of viral infection in a patient with heart disease, characterized in that the method comprises determining a free kappa light chain level and/or a free lambda light chain level of a specimen and comparing at least one value of the kappa chain level, the lambda chain level, and a kappa/lambda ratio with that of a healthy subject.

[3] A method for detecting severity of heart disease, characterized in that the method comprises determining a free kappa light chain level and/or a free lambda light chain level of a specimen and comparing at least one value of the kappa chain level, the lambda chain level, and a kappa/lambda ratio with that of a healthy subject or a patient suffering slight heart disease.

[4] A method as described in [1], [2], or [3] above, wherein the heart disease is heart failure, cardiomyopathy, myocarditis, or acute myocardial infarction.

[5] A method as described in [1], [2], or [3] above, wherein the free light chain levels are determined through immunoassay.

[6] A kit for diagnosing heart disease and for carrying out a method as recited in [1], [2], or [3] above, the kit comprising at least one reagent selected from the group consisting of a) to d):
  a) an immobilized FLC-specific antibody,
  b) a labeled FLC-specific antibody,
  c) an FLC-specific antibody, and
  d) a secondary antibody which can specifically bound to an antibody as recited in c) above.

[7] A kit as described in [6] above, wherein the heart disease is heart failure, cardiomyopathy, myocarditis, or acute myocardial infarction.

[8] A kit as described in [6] above, wherein the FLC levels are determined through immunoassay.

Effects of the Invention

The present invention has first elucidated that FLC is useful for the diagnosis of heart diseases such as heart failure, cardiomyopathy, myocarditis, and acute myocardial infarction. In addition, the invention has first elucidated that FLC is useful for the diagnosis of a complication of viral infection (e.g., infection with hepatitis C virus) in a patient with cardiomyopathy or myocarditis. Therefore, the method for detecting heart disease and the kit for diagnosing heart disease are remarkably useful for the diagnosis of heart disease as well as a complication of viral infection in a patient with heart disease.

In addition, since the kappa level and the lambda level correlate to the NT-proBNP level, which is useful for determination of severity and prediction of prognosis of heart diseases such as heart failure, FLC assay is useful for the determination of severity and prediction of prognosis of heart diseases such as heart failure.

Furthermore, the present invention realizes evaluation of the effects of a therapeutic drug for heart disease and that of an antiviral drug. Therefore, the invention is of great value in development of therapeutic agents for heart disease and viral infections.

BEST MODES FOR CARRYING OUT THE INVENTION

Figure 1:
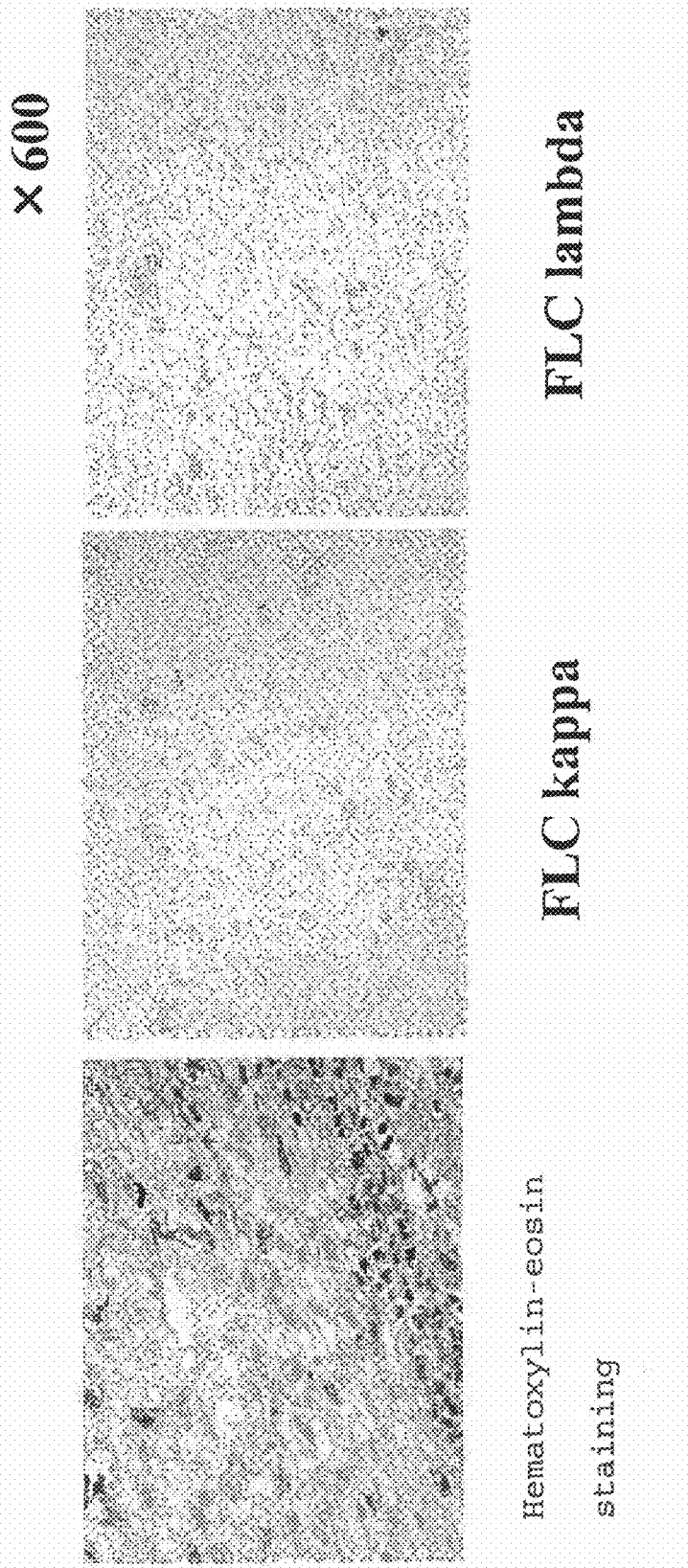
FIG. 1 Images showing detection of kappa chains or lambda chains in the cardiac muscular tissue suffering heart failure (hematoxylin-eosin stain, FLC kappa (kappa chain detection, and FLC lambda (lambda chain detection).

1. Method for Diagnosis of Heart Disease

As mentioned above, at least one FLC-related value of kappa chain level, lambda chain level, and kappa/lambda ratio reflects conditions and prognosis of heart disease. Therefore, heart disease can be diagnosed through quantitation of the free light chains (kappa chain and lambda chain) in specimens.

The specimen to be analyzed is blood, body fluid, tissue, excretions, etc. separated from subjects, clinical specimens, etc. Among these specimens, blood-originating specimens such as blood, serum, and plasma, and urine specimens are particularly preferred.

FLC assay may be performed through a known immunoassay technique (ELISA, RIA, etc.).

Specifically, in a preferred immunoassay procedure, a microamount of FLC present in a specimen can be determined at sufficient sensitivity, and no cross-reactivity to intact immunoglobulin is observed (e.g., $\leq 1\%$), whereby effects of components other than FLC can be minimized. Preferably, an enzymatic immunoassay method developed by Nakano et al. is employed (J. Immunol. Methods, 2003, 275, 9-17).

In order to determine FLC at higher sensitivity, preferably employed is an immunoassay method in which an FLC-specific polyclonal antibody is used as an antibody for trapping FLC in a specimen, and an FLC-specific monoclonal antibody is used as an antibody for detecting the trapped FLC.

The two types of antibodies employed in the invention are selected from FLC-specific monoclonal antibodies and FLC-specific polyclonal antibodies. Such antibodies may be antibodies per se or active fragments thereof [F(ab')$_2$, Fab', etc.].

The FLC-specific antibody refers to an antibody which exhibits very weak reactivity to a light chain bound to the heavy chain present in intact immunoglobulin or which does not recognize the light chain, but which strongly reacts with a light chain not bound to the heavy chain.

These FLC-specific monoclonal antibodies and polyclonal antibodies may be produced through a conventional method. For example, monoclonal antibodies are prepared by use of a free kappa chain or a free lambda chain as an antigen, and an antibody which does not bind to intact immunoglobulin and which specifically binds to FLC is selected from the thus-produced antibodies.

The FLC-specific polyclonal antibody may be produced through a conventional method. For example, polyclonal-antibodies are prepared by use of a free kappa chain or a free lambda chain, and an antibody which binds to intact immunoglobulin is absorbed and removed from the thus-produced polyclonal-antibodies. Such antibodies, which are now commercially available, may also be employed. However, FLC specificity of such commercial products must be checked in advance.

The immunoassay method employed in the invention is the same as conventionally employed method in terms of technique, procedure, etc. Specifically, examples of the antibody for trapping FLC in a specimen include an immobilized antibody fixed on a support.

Examples of the support employed for preparing such an immobilized antibody include generally employed supports, including synthetic organic polymer compounds such as polyvinyl chloride, polystyrene, styrene-divinylbenzene copolymers, styrene-maleic anhydride copolymers, nylon, polyvinyl alcohol, polyacrylamide, polyacrylonitrile, polypropylene, and polymethylene methacrylate; polysaccharides such as dextran derivatives (e.g., Sephadex), agarose gel (e.g., Sepharose or Biogel), and cellulose (e.g., paper disk or filter paper); and inorganic polymer compounds such as glass, silica gel, and silicone. Such a support may have an introduced functional group (e.g., an amino group, a carboxyl group, a carbonyl group, a hydroxyl group, or a sulfhydryl group).

Such a support may assume any form, such as a plate form (e.g., microtiter plate or disk), a particulate form (e.g., beads), a tubular form (e.g., test tube), a fibrous form, a membrane form, a microparticulate form (e.g., latex particles), a capsule form, or an endoplasmic reticulum form. A support of suitable form may be appropriately selected in consideration of the assay method employed.

Binding of an antibody to a support may be carried out through a known technique such as physical adsorption, ionic binding, covalent binding, or entrapment [see, for example, "Koteika Koso" ("Immobilized Enzyme") (edited by Ichiro Senhata, published by Kodansha Ltd. on Mar. 20, 1975)]. Particularly, physical adsorption is preferred, from the viewpoint of convenience. An antibody may be bound directly to a support, or a linker may be provided between an antibody and a support.

In order to suppress non-specific binding, the thus-prepared immobilized reagent may be subjected to blocking treatment by use of a generally employed blocking agent such as gelatin or BSA.

Examples of the antibody for detecting trapped FLCs include an antibody labeled with a labeling agent. Examples of labeling agents employed include radioisotopes such as $^{32}$P, $^3$H, $^{14}$C, and $^{125}$I; enzymes such as β-galactosidase, peroxidase, alkaline phosphatase, glucose-6-phosphate dehydrogenase, catalase, glucose oxidase, lactate oxidase, alcohol oxidase, and monoamine oxidase; coenzymes and prosthetic groups such as FAD, FMN, ATP, biotin, and heme; fluorescein derivatives such as fluorescein isothiocyanate and fluorescein thiofurbamyl; rhodamine derivatives such as tetramethylrhodamine B isothiocyanate; fluorescent dyes such as umbelliferone and 1-anilino-8-naphthalenesulfonate; and luminol derivarives such as luminol, isoluminol, and N-(6-aminohexyl)-N-ethylisoluminol.

Binding of an antibody to a labeling agent may be carried out through a method appropriately selected from among known methods described in the literature [for example, "Zoku Seikagaku Jikken Koza 5, Men-eki Seikagaku Kenkyu-ho" ("Sequel to Biochemical Experiments 5, Immunobiochemical Studies"), published by Tokyo Kagaku Dojin Co., Ltd. (1986), pp. 102-112].

Assay employing such an immobilized antibody and labeled antibody may employ a typical immunoassay procedure as it is. Specifically, an immobilized antibody is reacted with a test sample, followed by optional BF separation, and the resultant product is reacted with a labeled antibody (two-step method), or an immobilized antibody, a test sample, and a labeled antibody are reacted simultaneously (one-step method); and subsequently, FLCs contained in the sample are detected or quantitatively determined through a method which is known per se.

Details of immunoassay are described in, for example, the following references.

(1) "*Zoku Rajio Immunoassei*" ("Sequel to Radioimmunoassay") edited by Hiroshi Irie (published by Kodansha Ltd. on May 1, 1979)
(2) "*Koso Men-eki Sokutei-ho*" ("Enzyme Immunoassay") (2nd Edition) edited by Eiji Ishikawa, et al. (published by Igaku-Shoin Ltd. on Dec. 15, 1982)
(3) *Rinsho Byori* Extra Edition No. 53 "*Rinsho Kensa no tameno Immunoassei—Gijutsu to Oyo*—("Immunoassay for Clinical Tests—Techniques and Applications—") (published by The Clinical Pathology Press, 1983)
(4) "Biotechnology Encyclopedia" (published by CMC Publishing Co., Ltd. on Oct. 9, 1986)
(5) "Methods in ENZYMOLOGY Vol. 70" (Immunochemical techniques (Part A))
(6) "Methods in ENZYMOLOGY Vol. 73" (Immunochemical techniques (Part B))
(7) "Methods in ENZYMOLOGY Vol. 74" (Immunochemical techniques (Part C))
(8) "Methods in ENZYMOLOGY Vol. 84" (Immunochemical techniques (Part D: Selected Immunoassay))
(9) "Methods in ENZYMOLOGY Vol. 92" (Immunochemical techniques (Part E: Monoclonal Antibodies and General Immunoassay Methods))
[(5) to (9), published by Academic Press]

The pathological condition and prognosis of heart disease is diagnosed on the basis of at least one value of the thus-determined free kappa light chain level, free lambda light chain level, and kappa/lambda ratio.

Examples of the target heart disease include heart failure, cardiomyopathy, myocarditis, acute myocardial infarction, and these heart diseases concomitant with viral infection.

The diagnosis is performed by comparing at least one value of the free kappa light chain level, free lambda light chain level, and kappa/lambda ratio of a specimen of a patient with that of a healthy subject. The diagnosis realizes detection of heart disease, a complication of viral infection in a patient with heart disease, or severity of heart disease, as well as discrimination between acute myocardial infarction and myocarditis or heart failure.

As mentioned in Example 1 hereinbelow, the kappa chain level, the lambda chain level, and the kappa/lambda ratio vary in response to the pathological conditions and correlate to the response of conventional markers and conventional heart function indices.

Therefore, on the basis of the aforementioned values, heart disease, a complication of viral infection in a patient with heart disease, or severity of heart disease can be detected. The detection of heart disease includes differential diagnosis of heart failure, cardiomyopathy, myocarditis, and acute myocardial infarction.

2. Kit for Diagnosing Heart Disease

The kit of the present invention, for carrying out the aforementioned heart disease diagnosing method, includes, for example, the following reagents:

1) an immobilized FLC-specific antibody and
2) a labeled FLC-specific antibody.

The FLC-specific antibody for forming the immobilized FLC-specific antibody and the labeled FLC-specific antibody may be an FLC-specific monoclonal antibody or an FLC-specific polyclonal antibody. Two FLC-specific monoclonal antibodies may be used in combination, or an FLC-specific polyclonal antibody and an FLC-specific monoclonal antibody may be used in combination. Among them, a combination of an immobilized FLC-specific polyclonal antibody and a labeled FLC-specific monoclonal antibody is preferred, from the viewpoint of sensitivity.

Instead of a labeled FLC-specific antibody, a non-labeled FLC-specific antibody and a secondary antibody may be used. In this case, the kit includes the following reagents:

1) an immobilized FLC-specific antibody,
2) an FLC-specific antibody, and
3) a labeled anti-immunoglobulin antibody.

As is the above case, the immobilized FLC-specific antibody or the FLC-specific antibody may be a monoclonal antibody or a polyclonal antibody. A combination of an immobilized FLC-specific polyclonal antibody and an FLC-specific monoclonal antibody is preferred, from the viewpoint of sensitivity.

If required, in addition to the aforementioned reagents, the kit of the present invention includes an appropriate reagent, depending on the assay method, selected from among a color developing reagent, a reaction-terminating reagent, a standard antigen reagent, a sample pre-treating reagent, and other reagents.

EXAMPLES

The present invention will next be described by way of examples, which should not be construed as limiting the invention thereto.

(1) Serum Specimens

Serum specimens tested in the experiment were collected from healthy volunteers, heart failure patients, cardiomyopathy patients, and myocarditis patients.

(2) FLC-specific Monoclonal Antibody

An FLC-specific monoclonal antibody was produced through immunizing BALB/c mice with FLC (product of Bethyl laboratories, Montgomery, Tex.) (J. Immunol. Methods, 275, 9-17. (2003)). An F(ab')$_2$ fragment of the produced antibody was lebeled with horseradish peroxidase (HRP) (J. Histochem. Cytochem., 22, 1084-91. (1974)).

(3) FLC Assay

FLC assay was performed according to a description (J. Immunol. Methods, 2003, 275, 9-17). Specifically, a specimen or a standard concentration solution (each 100 μL) was added to a 96-well microplate (Nunc) coated with the FLC-specific monoclonal antibody, followed by reaction at room temperature for two hours. After washing, an HRP labeled anti-kappa light chain antibody or an HRP-labeled anti-lambda light chain antibody (each 100 μL) serving as secondary antibodies were added to the microplate, followed by reaction at 37° C. for 30 minutes. After reaction, the microplate was washed with PBS containing 0.05% Tween 20, and the reactions were allowed to develop color by dispensing to each well a color developing liquid (OPD, product of Sigma) (each 100 μL). The color development was terminated with 1N sulfuric acid, and absorbance at 492 nm was measured. In the assay, 50 mM Tris-HCl (pH 7.5) containing 1% bovine serum albumin was employed as a buffer.

Example 1

Heart failure patients (63) (from December 2002 to November 2004) were investigated as follows. Among the patients, 17 patients were investigated in terms of NT-proBNP level and stem cell factor (SCF) level, with correlation to FLC levels. The results are shown in Table 1.

TABLE 1

|  | NT-proBNP(y) | | | SCF(y) | | |
|---|---|---|---|---|---|---|
| X |  | $r^2$ | P |  | $r^2$ | p |
| Kappa | y = 280x − 4920 | 0.511 | 0.0013 | y = 12.9x + 381 | 0.3518 | 0.012 |
| Lambda | y = 51.6x − 455 | 0.806 | <0.0001 | y = 1.72x + 642 | 0.289 | 0.0259 |
| Kappa/lambda | y = −32600x + 18900 | 0.564 | 0.0005 |  | 0.0641 | 0.327 |

Example 2

Serum FLC levels determined in a multi-center clinical trial on myocarditis treatment are shown below.

(1) Table 2 shows serum FLC levels of all myocarditis patients.

TABLE 2

|  | n | kappa (mg/L) | lambda (mg/L) | kappa/lambda |
|---|---|---|---|---|
| Myocarditis | 1,318 | 37.6 ± 19.2** | 72.4 ± 124.2* | 0.64 ± 0.32 |
| Healthy subjects | 17 | 27.9 ± 5.3 | 43.6 ± 8.8 | 0.66 ± 0.16 |

Mean ± standard deviation,
*p < 0.0005,
**p < 0.0001

(2) Table 3 shows the effect of infection with hepatitis C virus (HCV) on FLC levels.

TABLE 3

|  | n | kappa (mg/L) | lambda (mg/L) | kappa/lambda |
|---|---|---|---|---|
| HCV (+) | 42 | 30.6 ± 14.8* | 173.1 ± 37.1* | 0.27 ± 0.22* |
| HCV (−) | 1,276 | 37.9 ± 19.3* | 69.1 ± 81.7* | 0.66 ± 0.31 |
| Healthy subjects | 17 | 27.9 ± 5.3 | 43.6 ± 8.8 | 0.66 ± 0.16 |

Mean ± standard deviation,
*p < 0.0001 with respect to healthy subject,
HCV (+, −),
p < 0.0001

(3) Table 4 shows FLC levels of hepatitis C virus antibody-positive cardiomyopathy patients.

TABLE 4

|  | n | kappa | lambda | kappa/lambda |
|---|---|---|---|---|
| Hepatitis C virus antibody (+) | 5 | 42.5 ± 27.2* | 79.9 ± 74.0* | 0.558 ± 0.338 |
| Healthy subjects | 17 | 27.9 ± 5.3 | 43.6 ± 8.8 | 0.661 ± 0.162 |

*p < 0.05

(4) Relationship between FLC levels and severity of heart failure

The tested subjects were classified into two categories in terms of severity (slight (grades I+II) and severe (grades III+IV)). Each grade denotes a heart function status on the basis of subjective symptoms graded by the New York Heart Association (NYHA). The results are shown in Table 5.

TABLE 5

|  | NYHA heart function scale | | |
|---|---|---|---|
|  | Slight (grades I + II) (n = 17) | Severe (grades III + IV) (n = 63) | p |
| Kappa | 32.0 ± 15.4 | 40.8 ± 39.2 | NS |
| Lambda | 55.0 ± 44.0 | 93.2 ± 67.9 | 0.03 |
| Kappa/lambda | 0.67 ± 0.31 | 0.46 ± 0.14 | 0.0001 |

(5) Results of Examples 1 and 2

(5-1) The kappa and lambda levels of heart failure patients positively correlated to NT-proBNP level, which relates to severity and prognosis of heart failure. The lambda level strongly correlated to NT-proBNP level, whereas the kappa/lambda ratio negatively correlated to NT-proBNP level.

(5-2) The kappa and lambda levels of heart failure patients positively correlated to the SCF level.

(5-3) The kappa and lambda levels of myocarditis patients increased, whereas the kappa/lambda ratio was unchanged.

(5-4) The kappa and lambda levels of myocarditis patients positively correlated to NT-proBNP level, whereas the kappa/lambda ratio negatively correlated to NT-proBNP level.

(5-5) The kappa and lambda levels of myocarditis patients concomitant with infection with hepatitis C virus increased. Of these, the lambda level considerably increased, and the kappa/lambda ratio considerably decreased.

(5-6) The kappa and lambda levels of cardiomyopathy patients positive to infection with hepatitis C virus increased, whereas the kappa/lambda ratio tended to decrease.

(5-7) Severe heart failure patients exhibited a lambda level higher than that of slight heart failure patients. The kappa/lambda ratio of severe heart failure patients decreased. Thus, the lambda level and the kappa/lambda ratio of heart failure patients reflect the severity of heart failure.

(5-8) The lambda level in heart failure concomitant with infection with hepatitis C virus further elevated but the kappa/lambda ratio lowered.

Example 3

Heart failure patients (48) were investigated as follows.

(1) The free kappa light chain level, free lambda light chain level, and kappa/lambda ratio of heart failure patients (48) were compared with those of healthy subjects (17).

The study has revealed that, in heart failure patients, the free lambda light chain level increases, and the kappa/lambda ratio decreases.

TABLE 6

|  | n | kappa | lambda | kappa/lambda |
|---|---|---|---|---|
| Heart failure | 48 | 32.7 ± 0.5 | 80.2 ± 57.5* | 0.46 ± 0.12** |
| Healthy subjects | 17 | 27.9 ± 5.3 | 43.6 ± 8.8 | 0.66 ± 0.16 |

Mean ± standard deviation, t-test,
*$p < 0.05$,
**$p < 0.0001$ (2) The relationship between survival time and FLC levels in heart failure patients (48) was investigated.

The study has revealed that a negative correlation is found between the survival time and the lambda chain level.

TABLE 7

|  |  | Survival time (day) (y) | | |
|---|---|---|---|---|
| X |  | r | $r^2$ | p |
| Lambda | y = −6.2x + 1010 | −0.48 | 0.23 | $p < 0.05$ |

(3) The relationship between the free kappa light chain level, free lambda light chain level, and kappa/lambda ratio and the NT-proBNP (product of Roche Diagnostics) level, which serves as an index for heart failure and myocardial disorders was investigated.

The study has revealed that the kappa chain and lambda chain levels exhibit positive correlation to the NT-proBNP level but negative correlation to the kappa/lambda ratio. Thus, these FLC levels can serve as an index for heart failure and myocardial disorders.

TABLE 8

|  |  | NT-proBNP (pg/mL) (y) | | |
|---|---|---|---|---|
| X |  | r | $r^2$ | p |
| Kappa | y = 246x − 3290 | 0.40 | 0.16 | $p < 0.005$ |
| Lambda | y = 54.7x + 341 | 0.49 | 0.24 | $p < 0.0005$ |
| Kappa/lambda | y = −18800x + 13300 | −0.36 | 0.13 | $p < 0.05$ |

(4) The relationship between the free kappa light chain level, free lambda light chain level, and kappa/lambda ratio and the pulmonary arterial pressure determined by means of cardiac catheterization was investigated.

The kappa chain and lambda chain levels exhibited positive correlation to the mean pulmonary arterial pressure.

TABLE 9

|  |  | Mean pulmonary arterial pressure (mmHg) (y) | | |
|---|---|---|---|---|
| X |  | r | $r^2$ | p |
| Kappa | 0.71x + 8.7 | 0.54 | 0.30 | $p < 0.05$ |
| Lambda | 0.22x + 14 | 0.48 | 0.23 | $p < 0.05$ |

(5) The relationship between the free kappa light chain level, free lambda light chain level, and kappa/lambda ratio and the cardiac output determined by means of cardiac catheterization was investigated.

The kappa chain and lambda chain levels exhibited significant negative correlation to the cardiac output, thereby revealing that these FLC levels relate to heart functions.

TABLE 10

|  |  | Cardiac output (L/m$^2$) (y) | | |
|---|---|---|---|---|
| X |  | r | $R^2$ | p |
| Kappa | y = −0.4x + 4.19 | −0.78 | 0.61 | $p < 0.0001$ |
| Lambda | y = −0.1x + 3.74 | −0.59 | 0.35 | $p < 0.005$ |

(6) The relationship between the free kappa light chain level, free lambda light chain level, and kappa/lambda ratio and the left venticular internal dimension in systole (LVDs), left venticular internal dimension in diastole (LVDd), and ejection fraction (EF) serving as an index for cardiac systolic function, which were determined by means of an ultrasonic cardiogram was investigated.

The lambda chain level was found to exhibit significant positive correlation to LVDd and LVDs and thus is conceived to be related to dimension of left venticular cavity. The kappa/lambda ratio was found to exhibit negative correlation to LVDd and LVDs and positive correlation to EF and thus is conceived to be related to dimension of left venticular cavity and cardiac systolic function.

TABLE 11

| X |  | R | $r^2$ | P |
|---|---|---|---|---|
|  |  | LVDd (mm) (y) | | |
| Kappa | y = 0.41x + 62.8 | 0.25 | 0.06 | p = 0.24 |
| Lambda | y = 0.33x + 51.3 | 0.58 | 0.33 | $p < 0.005$ |
| Kappa/lambda | y = −98x + 119 | −0.72 | 0.51 | $p < 0.0001$ |
| Kappa | y = 0.42x + 52.1 | 0.25 | 0.06 | p = 0.24 |
| Lambda | y = 0.33x + 40.8 | 0.57 | 0.32 | $p < 0.005$ |
| Kappa/lambda | y = −102x + 110 | −0.73 | 0.53 | $p < 0.0001$ |
|  |  | EF (%) (y) | | |
| Kappa/lambda | y = 67.4x − 0.14 | 0.59 | 0.35 | $p < 0.005$ |

(7) The correlation of the free kappa light chain level, free lambda light chain level, and kappa/lambda ratio to the CRP level serving as an index for inflammatory reaction was investigated.

The kappa chain and lambda chain levels were found to exhibit significant positive correlation to the CRP level and reflect inflammatory reaction.

TABLE 12

|  |  | CRP (mg/dL) (y) | | |
|---|---|---|---|---|
| X |  | R | $r^2$ | P |
| Kappa | y = 0.3x − 6.89 | 0.5 | 0.25 | $p < 0.05$ |
| Lambda | y = 0.95x − 4.54 | 0.46 | 0.21 | $p < 0.05$ |
| Kappa/lambda | y = −7.8 + 5.73 | −0.16 | 0.02 | p = 0.46 |

(8) The correlation of the free kappa light chain level, free lambda light chain level, and kappa/lambda ratio to the type IV collagen level, serving as an index for fibrogenesis was investigated.

The kappa chain and lambda chain levels were found to exhibit positive correlation to the type IV collagen level, and the kappa/lambda ratio exhibit negative correlation to the type IV collagen level. Thus, FLC levels were found to be related to a marker for fibrogenesis.

TABLE 13

| X | | R | $r^2$ | P |
|---|---|---|---|---|
| | | Type IV collagen (ng/mL) (y) | | |
| Kappa | y = 0.48x + 20.5 | 0.62 | 0.39 | p < 0.0001 |
| Lambda | y = 1.1x + 89.3 | 0.78 | 0.61 | p < 0.0001 |
| Kappa/lambda | y = −250x + 291 | −0.38 | 0.14 | p < 0.01 |

(9) Paraffin sections of cardiac muscular specimens of heart failure patients were stained with hematoxylin-eosin, and the diameters of cardiac muscular cells were measured, and the relationship between cell diameter and FLC level was investigated.

The cardiac muscular cell diameter was found to exhibit negative correlation to the kappa/lambda ratio.

TABLE 14

| x | | R | $r^2$ | P |
|---|---|---|---|---|
| | | Cardiac muscular cell diameter (μm) (y) | | |
| Kappa/lambda | y = −31.8x + 44.9 | −0.63 | 0.39 | p < 0.005 |

(10) The relationship between the FLC levels and the activity of mast cells was investigated. RNA was extracted from cardiac muscular tissue specimens which had been sampled during surgery of a heart failure patient and preserved in a frozen state. Through real-time PCR, expression of mRNAs of stem cell factor (SCF), metalloprotease (MMP-9), chymase, and tryptase was investigated. The amount of each expressed mRNA was corrected by a housekeeping gene, GAPDH.

The kappa/lambda ratio was found to exhibit positive correlation to the expression amount of SCF, MMP-9, chymase, and tryptase and is conceived to be related to activation of mast cells.

TABLE 15

| x | | R | $r^2$ | P |
|---|---|---|---|---|
| | | SCF/GAPDH (y) | | |
| Kappa/lambda | y = 12900x − 4590 | 0.46 | 0.21 | p < 0.05 |
| | | MMP-9/GAPDH (y) | | |
| Kappa/lambda | y = 651x − 231 | 0.44 | 0.19 | p < 0.05 |
| | | Chymase/GAPDH (y) | | |
| Kappa/lambda | y = 349x − 124 | 0.43 | 0.19 | p < 0.05 |
| | | Tryptase/GAPDH (y) | | |
| Kappa/lambda | y = 1050x − 373 | 0.43 | 0.18 | p < 0.05 |

(11) Distribution of bound kappa chains and lambda chains in the cardiac muscular tissue of a heart failure patient was investigated.

Specifically, slices of 5 micrometers square were cut out of a paraffin block of a formalin-fixed specimen of the heart suffering heart failure. Each slice was deparaffinized with xylene, dehydrated with alcohol, and treated with hydrogen peroxide for inactivating endogenous peroxidase.

The heart specimens were incubated with Mouse monoclonal antibodies (products of Yamasa corporation, Chiba) to a kappa chain and to a lambda chain, serving as a primary antibody, overnight at 4° C., and immunostained by means of a Vectastain ABC kit (Burlingame, Calif., U.S.A.) for mouse IgG, followed by color development with DAB.

As shown in FIG. 1, kappa chains and lambda chains were observed in leucocytes in the cardiac muscular tissue suffering heart failure. Thus, leucocytes infiltrating the cardiac muscular tissue were found to produce kappa chains and lambda chains.

(12) Urine FLC levels of heart failure patients (20) were determined, and the determined values were compared with those of healthy subjects.

In heart failure patients, the urine kappa chain and lambda chain levels were significantly higher than those of the healthy subjects.

TABLE 16

| | n | kappa (mg/L) | lambda (mg/L) | kappa/lambda |
|---|---|---|---|---|
| Healthy subjects | 29 | 2.14 ± 2.34 | 2.79 ± 3.49 | 0.82 ± 0.29 |
| Heart failure | 20 | 5.74 ± 7.56* | 7.10 ± 8.75* | 0.82 ± 0.29 |

*p < 0.05 with respect to healthy subjects

(13) Correlation of urine FLC levels to blood FLC levels in heart failure patients (20) was investigated.

Significant positive correlation was observed between the urine kappa chain level, lambda chain level, and kappa/lambda ratio and the blood kappa chain level, lambda chain level, and kappa/lambda ratio.

TABLE 17

| | N | r | $r^2$ | P |
|---|---|---|---|---|
| Urine kappa (y):blood kappa (x) | y = 0.165x − 6.28 | 0.45 | 0.20 | p < 0.05 |
| Urine lambda (y):blood lambda (x) | y = 0.0936x − 3.5 | 0.58 | 0.34 | p < 0.01 |
| Urine kappa/lambda (y):blood kappa/lambda (x) | y = 0.922x + 0.156 | 0.65 | 0.42 | p < 0.005 |

(14) Results of Example 3

(14-1) In heart failure patients, the lambda chain level increased, and the kappa/lambda ratio decreased.

(14-2) The lambda chain level related to prognosis (survival time) of heart failure patients.

(14-3) The kappa chain and lambda chain levels correlated to NT-proBNP level, which is a marker for heart failure and for myocardial disorders, and to CRP level, which is a marker for inflammation.

(14-4) The kappa chain and lambda chain levels related to cardiac functions, and the lambda chain level and the kappa/lambda ratio correlated to dimension of intracardiac cavity.

(14-5) The kappa chain and lambda chain levels and the kappa/lambda ratio correlated to the level of fibrogensis marker.

(14-6) The kappa/lambda ratio reversely correlated to hypertrophy of myocardial cells.

(14-7) The kappa/lambda ratio correlated to the level of mast-cell-related mediators.

(14-8) Leucocytes infiltrating the cardiac muscular tissue suffering heart failure produced kappa chains and lambda chains.

(14-9) Urine kappa chain and lambda chain levels of heart failure patients increased.

(14-10) The urine kappa chain level, lambda chain level, and kappa/lambda ratio of heart failure patients correlated to the blood kappa chain level, lambda chain level, and kappa/lambda ratio.

Example 4

FLC levels of acute myocardial infarction patients were measured in the onset day, 24 hours after, and four weeks after, and these values were compared with those of healthy subjects.

The kappa chain levels of the patients significantly decreased on the day of myocardial infarction onset and 24 hours after. However, no significant difference was found in the lambda chain level and the kappa/lambda ratio between the patients and the healthy subjects.

Thus, the measurement of the free kappa light chain level is useful for the diagnosis of acute myocardial infarction and also for the differential diagnosis of acute myocardial infarction from myocarditis and heart failure.

TABLE 18

|  | n | kappa (mg/L) | lambda (mg/L) | kappa/lambda |
|---|---|---|---|---|
| Healthy subjects | 17 | 27.9 ± 5.3 | 43.6 ± 8.8 | 0.66 ± 0.16 |
| Acute heart infarction | | | | |
| Onset day | 70 | 23.6 ± 8.3* | 50.2 ± 40.5 | 0.54 ± 0.20 |
| 24 hours | 65 | 22.5 ± 6.8* | 48.7 ± 42.5 | 0.56 ± 0.23 |
| 4 weeks | 36 | 27.4 ± 7.8 | 53.6 ± 19.8 | 0.53 ± 0.14 |

One-way analysis of variance: F = 5.0;
$p < 0.005$
Intergroup comparison: Fisher's LDS,
*$p < 0.05$ (vs. healthy subjects, 4 weeks after)

As described hereinabove, FLC level measurement is useful for the diagnosis of heart failure, cardiomyopathy, myocarditis, and acute myocardial infarction. Since the kappa chain and lambda chain levels increase and the kappa/lambda ratio decreases in patients suffering cardiomyopathy or myocarditis concomitant with infection with hepatitis C virus, FLC levels are useful for the diagnosis of infection of such patients with hepatitis C virus and other viruses.

In heart failure patients concomitant with HCV infection, the lambda level further increases and the kappa/lambda ratio decreases, as compared with heart failure patients not infected with HCV. Therefore, coexistence of infection in a patient can be diagnosed.

According to the present invention, the effects of a heart failure therapeutic drug and an anti-viral drug can be evaluated. Therefore, the invention is of great value in development of therapeutic agents for heart failure, cardiomyopathy, and myocarditis as well as viral infections.

Severe heart failure patients exhibited a lambda level higher than that of slight heart failure patients. The kappa/lambda ratio of severe heart failure patients decreased. Thus, the lambda level and the kappa/lambda ratio correlated to the severity of heart failure. In addition, since the kappa chain and lambda chain levels correlate to the severity of heart failure and to the NT-proBNP level, which is a useful index for prognosis of heart failure, FLC level measurement is useful for evaluation of severity and prognosis of heart failure.

The invention claimed is:

1. A method for detecting a complication of hepatitis C viral infection in a patient with heart disease, comprising
    determining a free immunoglobulin kappa light chain level and a free immunoglobulin lambda light chain level of a specimen from said patient; and
    comparing at least one value of the kappa chain level, the lambda chain level, and a kappa/lambda ratio with that of a healthy subject, wherein an increase in the lambda chain level relative to a healthy subject or a decrease in the kappa/lambda ratio is indicative of a complication of viral infection in the patient,
    wherein the heart disease is heart failure, cardiomyopathy, myocarditis, or acute myocardial infarction.

2. A method for detecting severity of heart disease, comprising
    determining a free immunoglobulin kappa light chain level and a free immunoglobulin lambda light chain level of a specimen;
    and comparing at least one value of the kappa chain level, the lambda chain level, and a kappa/lambda ratio with that of a healthy subject or a patient suffering slight heart disease, wherein an increase in the lambda chain level relative to a healthy subject or a decrease in the kappa/lambda ratio is indicative of severity of heart disease,
    wherein the heart disease is heart failure, cardiomyopathy, myocarditis, or acute myocardial infarction.

3. The method of claim 1, wherein the free immunoglobulin light chain levels are determined through immunoassay.

4. The method of claim 2, wherein the free immunoglobulin light chain levels are determined through immunoassay.

5. The method of claim 1, comprising comparing at least one value of the lambda chain level, and a kappa/lambda ratio with that of a healthy subject.

6. The method of claim 2, comprising comparing at least one value of the lambda chain level, and a kappa/lambda ratio with that of a healthy subject.

7. The method of claim 1, wherein the lambda chain level is compared with that of a healthy subject.

8. The method of claim 1, wherein the kappa/lambda ratio is compared with that of a healthy subject.

9. The method of claim 2, wherein the lambda chain level is compared with that of a healthy subject.

10. The method of claim 2, wherein the kappa/lambda ratio is compared with that of a healthy subject.

11. The method of claim 1, wherein the specimen is a blood specimen, a serum specimen, a plasma specimen or a urine specimen.

12. The method of claim 2, wherein the specimen is a blood specimen, a serum specimen, a plasma specimen or a urine specimen.

* * * * *